(12) United States Patent
Mena

(10) Patent No.: US 7,137,817 B2
(45) Date of Patent: Nov. 21, 2006

(54) IMPLANT FIXATION DEVICE

(75) Inventor: Raul R. Mena, Plantation, FL (US)

(73) Assignee: Quantum Bioengineering, Ltd., Plantation, FL (US)

( * ) Notice: Subject to any disclaimer, the term of this patent is extended or adjusted under 35 U.S.C. 154(b) by 0 days.

(21) Appl. No.: 10/026,667

(22) Filed: Dec. 21, 2001

(65) Prior Publication Data

US 2002/0102518 A1    Aug. 1, 2002

Related U.S. Application Data

(60) Provisional application No. 60/258,261, filed on Dec. 22, 2000.

(51) Int. Cl.
  *A61C 8/00* (2006.01)
  *A61F 2/30* (2006.01)
(52) U.S. Cl. .......................... 433/174; 606/65
(58) Field of Classification Search ................ 433/173, 433/174; 606/65
  See application file for complete search history.

(56) References Cited

U.S. PATENT DOCUMENTS

| | | | |
|---|---|---|---|
| 4,177,524 A | * | 12/1979 | Grell et al. |
| 4,466,796 A | * | 8/1984 | Sandhaus ..................... 433/173 |
| 5,022,860 A | * | 6/1991 | Lazzara et al. ............. 433/174 |
| 5,061,181 A | * | 10/1991 | Niznick ....................... 433/174 |
| 5,338,197 A | * | 8/1994 | Kwan .......................... 433/174 |
| 6,036,491 A | * | 3/2000 | Hansson ....................... 433/174 |
| 6,234,797 B1 | * | 5/2001 | Ura ............................. 433/174 |

OTHER PUBLICATIONS

"Bicon Dental Implants", Catalogue and Clinical Technique Manual, 1996, 3 pgs.
"Screw-Vent Implants and Surgical Instruments", 3 pgs.
"Simpler Implants", 4 pgs.
"Self-tapping Fixtures", 1 pg.
"New Star/Vent Multi-Purpose Implant Screws", 2 pgs.
"IMPLA-MED Surgical Implant Components", 1 pg.
"Swede-Vent", 4 pgs.
"Replace Implant System", 1 pg.
"Titanodont Subcortical Implant System", 5 pgs.

* cited by examiner

Primary Examiner—Cary E. O'Connor
(74) Attorney, Agent, or Firm—Christopher & Weisberg, P.A.

(57) ABSTRACT

A fixation device at least partially implantable into tissue has a shaft having an outer face and a threaded portion wound around the outer face and forming a helical groove. At least a part of the threaded portion is implantable into tissue. The threaded portion includes a first face, a second face and a third face. The first face has a first end portion in curved contact with the outer face and a second end portion opposite the first end portion. The second face has a third end portion in curved contact with the outer face and a fourth end portion opposite the third end portion. The third face is coupled to the second end portion and the fourth end portion and is substantially parallel with the outer face.

3 Claims, 3 Drawing Sheets

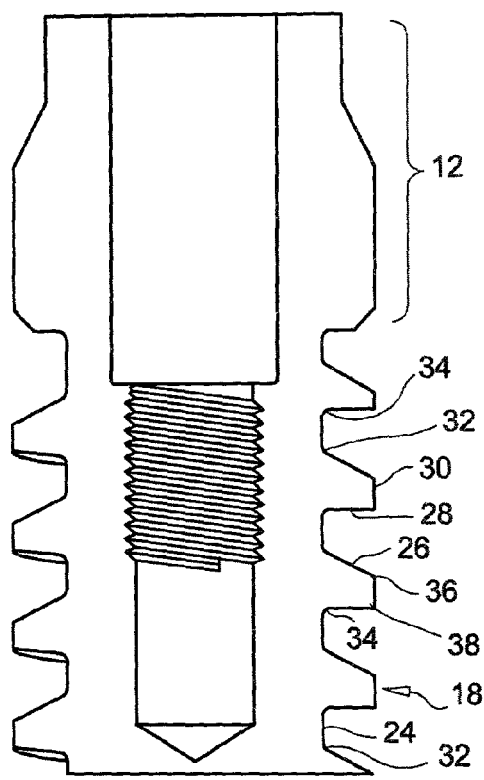
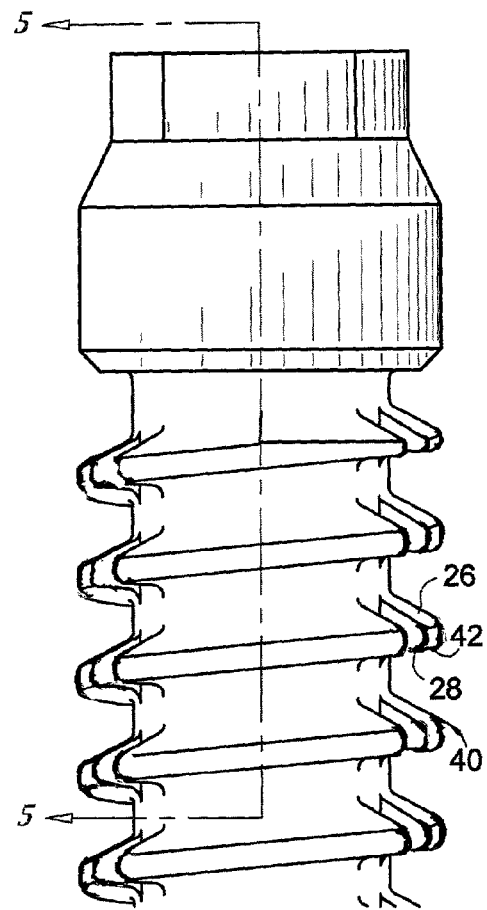
Fig. 3
Fig. 4

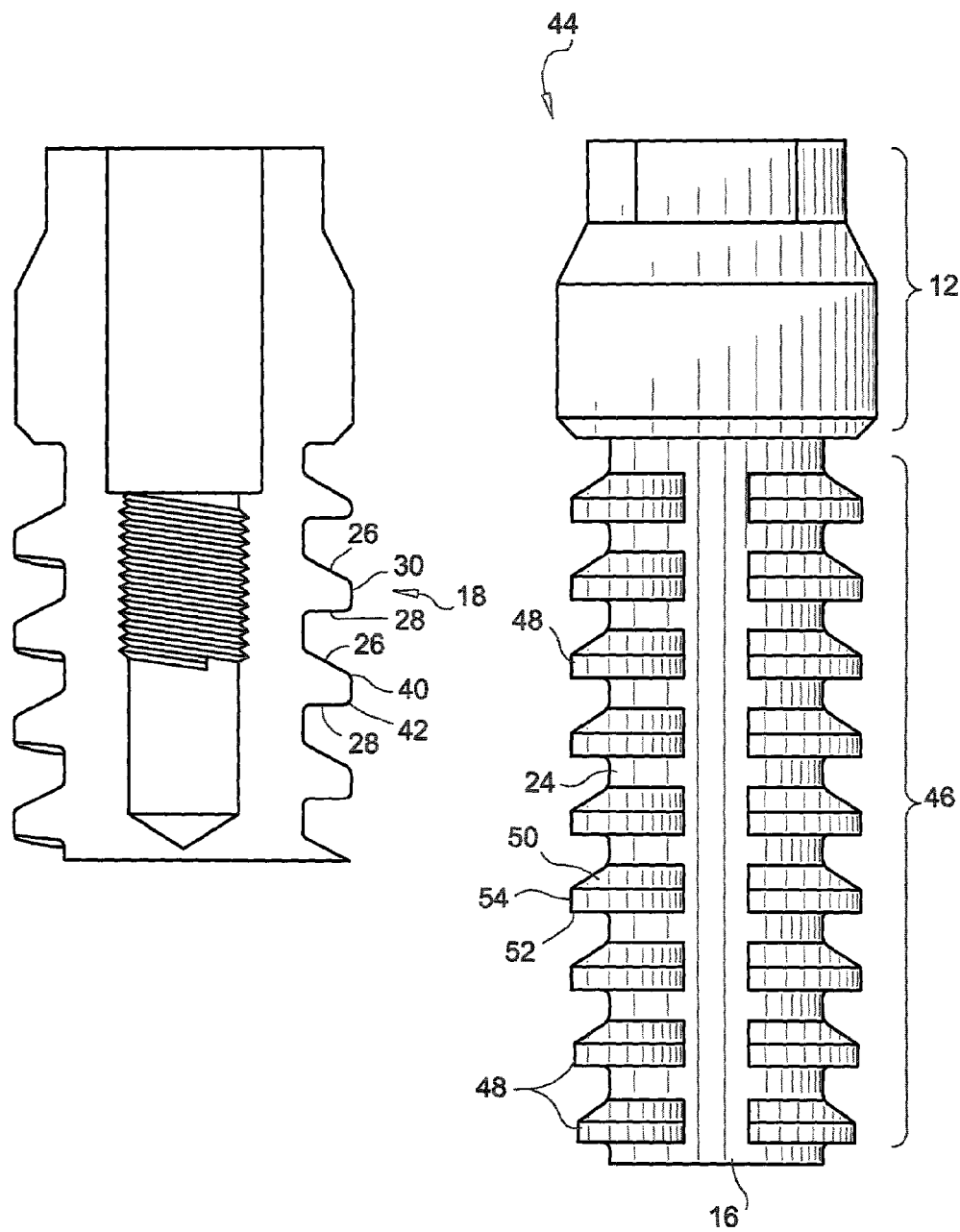
*Fig. 5*     *Fig. 6*

IMPLANT FIXATION DEVICE

CROSS-REFERENCE TO RELATED APPLICATION

This application is related to and claims priority to U.S. Provisional Application Ser. No. 60/258,261, filed Dec. 22, 2000, entitled DENTAL IMPLANT FIXATION, the entirety of which is incorporated herein by reference.

STATEMENT REGARDING FEDERALLY SPONSORED RESEARCH OR DEVELOPMENT n/a

FIELD OF THE INVENTION

The present invention relates to tissue implants, and in particular, to fixation elements for dental and orthopedic implants.

BACKGROUND OF THE INVENTION

Humans have a long history of having dental problems. Toothaches and the premature loss of teeth are recorded among our earliest written histories. History reflects the knowledge of the name of an Egyptian dentist who treated the Pharaoh's teeth around 3000 BC. In the early 1950's, it became known that living bone could grow and bond with certain metals such as titanium and the start of the modem use of dental implants started in earnest.

Although dental implants generally function as well as natural teeth, there are problems associated with the dental implants commonly used.

The strongest muscles in humans are known as the masseters. Masseters are located on the sides of your mouth and can exert a force of approximately 160 lbs. As such, teeth must be able to stand up to this kind of force when tearing and chewing food. Dental implants must also be able to function under this load. Implants are known to break when the force on the implanted tooth exceeds the mechanical limit of the implant material.

The stresses applied to implants during the normal course of eating include both compression as well as shear forces. Because the metal used to make implants must be machined, weaknesses are introduced into the implants that can lead to their failure. An example of a dental implant device is described in U.S. Pat. No. 5,533,898, issued to Mena, the entire contents of which are incorporated by reference herein. Replacing a broken implant is an expensive and serious undertaking. Additionally, stress can be transferred to the bone surrounding the implant causing pain, or fractures of the jaw, and bone resorption which can be even more serious than implant breakage. There is a need for a dental implant that has improved shear force resistance that is easy to machine without introducing unacceptable stress points in either the implant or the bone in which it is implanted.

Similar problems are exhibited with orthopedic implants. In particular, the compression and sheer forces placed on orthopedic implants can cause the implants to break, or cause bone resorption or procedure failure necessitating additional painful and expensive surgeries. It is therefore desirable to have an implant suitable for orthopedic use which, like the desired dental implant, has improved shear force resistance over prior art orthopedic implants and is easy to machine without introducing unacceptable stress points in either the implant or the bone in which it is implanted.

SUMMARY OF THE INVENTION

An aspect of the present invention provides a fixation device at least partially implantable into tissue in which a shaft has an outer face. A threaded portion wound around the outer face forms a helical groove in which at least a part of the threaded portion is implantable into tissue. The threaded portion has a first face, a second face and a third face. The first face has a first end portion in curved contact with the outer face and a second end portion opposite the first end portion. The second face has a third end portion in curved contact with the outer face and a fourth end portion opposite the third end portion. The third face is coupled to the second end portion and the fourth end portion and is substantially parallel with the outer face.

According to another aspect, the present invention provides a dental implant at least partially implantable into oral tissue, in which a shaft has an outer face. A threaded portion wound around the outer face forms a helical groove in which at least a part of the threaded portion is implantable into the oral tissue. The threaded portion has a first face, a second face and a third face. The first face has a first end portion in curved contact with the outer face and a second end portion opposite the first end portion. The second face has a third end portion in curved contact with the outer face and a fourth end portion opposite the third end portion. The third face is coupled to the second end portion and the fourth end portion and is substantially parallel with the outer face.

According to still yet another aspect, the present invention provides a fixation device at least partially implantable into tissue in which a shaft has an outer face. A plurality of fin sections are disposed along at least a portion of the length of the other face in which each of the fin sections is coaxial with the shaft and has a diameter greater than the diameter of the outer face at the disposed location. Each of the fin sections has a first face, a second face and a third face. The first face has a first end portion in curved contact with the outer face and a second end portion opposite the first end portion. The second face has a third end portion in curved contact with the outer face and a fourth end portion opposite the third end portion. The third face is coupled to the second end portion and the fourth end portion and is substantially parallel with the outer face.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is a section view taken along section line 3—3 in FIG. 2;

FIG. 4 is an enlarged view of an alternate arrangement of an engagement section and a portion of an anchorage section of the implant device shown in FIG. 1;

FIG. 5 is a section view taken along section line 5—5 in FIG. 4; and

FIG. 6 is a view showing an alternate arrangement of an implant device constructed in accordance with the principles of the present invention.

DETAILED DESCRIPTION OF THE INVENTION

Figure 1:
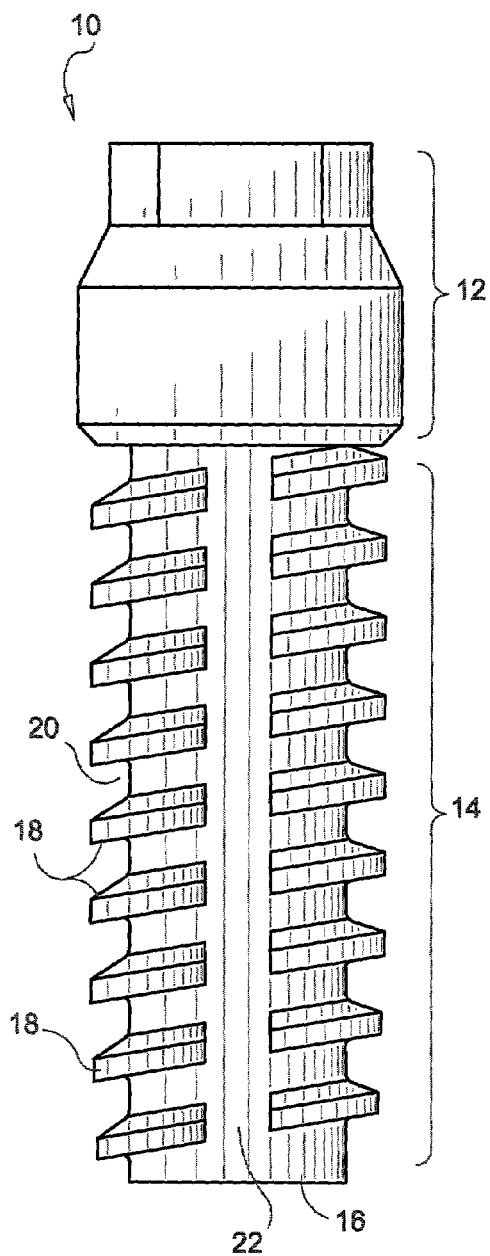
FIG. 1 is a view of an implant device constructed in accordance with the principles of the present invention.

Referring now to the drawing figures in which like reference designators refer to like elements, there is shown in FIG. 1 an implant device constructed in accordance with the principles of the present invention and designated generally as 10. Implant device 10, engagement section 12, and anchorage section 14 are preferably constructed as a single unit and made from a suitable material such as titanium. Anchorage section 14 includes a shaft 16 around which is wound threads forming a threaded portion 18. A helical groove 20 is provided between the threads. Threaded portion 18 also has at least one transverse slot 22 along at least a portion of the thread 18. Slot 22 advantageously provides additional surface area for bonding between device 10 and the tissue and provides a path for blood and tissue matter to escape during the insertion and healing period.

Threaded portion 18 is preferably formed as an integral unit with shaft 16. In use, at least a portion of anchorage section 14 is implanted by a screwing motion into the patient's tissue such that the threaded portion 18 engages with the tissue to hold the implant device in place. Engagement section 12 protrudes from the tissue into the oral cavity or is submerged into the bone structure in the case of a dental implant and is adapted to couple with a suitable abutment member (not shown). Implant devices constructed in accordance with the principles of the present invention are suitable for use as dental implants and orthopedic implants, the main difference between the two types being the dimensions of the devices. Dimensions which have been determined to be advantageous to each of these types are described below in detail.

Figure 2:
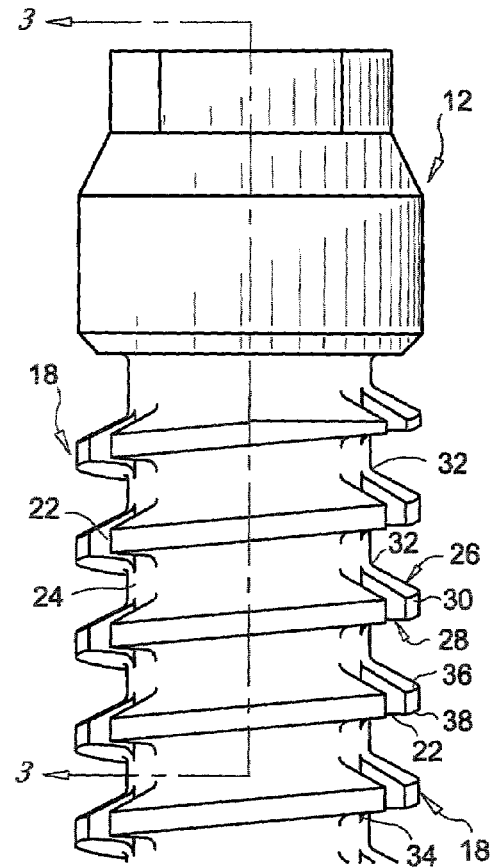
FIG. 2 is an enlarged view of an engagement section and a portion of an anchorage section of the implant device shown in FIG. 1.

Referring now to FIG. 2, there is shown an enlarged view of engagement section 12 along with a portion of anchorage section 14. As shown in FIG. 2, threaded portion 18 is coupled to outer face 24 and includes an upper face 26 and lower face 28 coupled to side face 30 at respective end portions thereof. Preferably, side face 30 is arranged to be substantially parallel with outer face 24. It has been found that the implant device has improved shear and tensile strength over prior art devices as a result of the substantially parallel nature between side face 30 and outer face 24. When lateral forces are applied, it allows forces to load under compression.

Upper face 26, at the end portion opposite the end portion that couples upper face 26 to side face 30, is in curved contact with outer face 24 and is shown as upper curved contact region 32. Upper curved contact region 32 is rounded and is defined by a radius. Similarly, lower curved contact region 34 is provided at the region of contact between lower face 28 and outer face 24. It has been found that providing curved contact regions 32 and 34 on anchorage section 14 provides superior strength to device 10 to prevent device 10 from shearing. Additionally, the curved surface is more likely to be filled by bone in-growth to create a more robust fixation of the implant and it decreases stress risers on the metal and stress concentration in the bone.

FIG. 3 is a section view taken along section line 3—3 in FIG. 2. FIG. 3 shows an enhanced view of threaded portion 18 and the relationship between the various faces and curved contact regions. As shown in FIG. 3, upper face 26 extends outwardly and downwardly from outer face 24, while lower face 28 is almost perpendicular to side face 30. It has been advantageously found that superior strength is provided by device 10 when the angle formed by the plane of outer face 24 and the plane of lower face 28 is between approximately 85 degrees and approximately 125 degrees. Similarly, it has been advantageously found that superior strength results when the angle formed by the plane of outer face 24 and the plane of upper face 26 is between approximately 95 degrees and approximately 140 degrees.

A significant improvement in the strength of the present invention over prior art devices has been found where the radius of upper curved contact region 32 is at least 0.08 and the radius of lower curved contact region 34 is at least 0.15.

The following dimensions have also been advantageously determined to provide an improvement over prior art devices for dental and orthopedic use. The width of threaded portion 18, i.e. the distance between the plane of outer face 24 and the plane of the substantially parallel side face 30 is between approximately 0.25 mm and approximately 3.00 mm for dental and 0.25 mm and 6.0 mm for orthopedic use. For the dental implant, the distance between upper face 26 and lower face 28 measured at approximately the curved contact regions 32 and 34 is 0.20 mm to 2.00 mm. For orthopedic implants, this distance is approximately 0.2 mm to approximately 6.00 mm. The distance between upper face 26 and lower face 28 at the other end portion of threads 18, namely the width of groove 20 measured at side face 30, is advantageously found to be between approximately 0.30 mm to approximately 3.00 mm for dental implants and 0.30 mm to 8.0 mm for orthopedic implants. The width of side face 30 has been found to provide the advantageous strength characteristics embodied in the present invention when the length of side face 30 is between approximately 0.25 mm to approximately 3.00 mm for dental implants and approximately 0.25 mm to 6.00 mm for orthopedic implants.

FIGS. 4 and 5 show views of device 10 which are similar to those shown and described with respect to FIGS. 2 and 3 respectively. As such, only the differences are described. In FIGS. 2 and 3, upper face 26 and lower face 28 are substantially planar at the end portion which contacts side face 30. As such, upper face 26 and lower face 28 meet side face 30 at points 36 and 38, respectively. As shown in FIGS. 4 and 5, the region at which upper face 26 and lower face 28 contact side face 30 is curved, shown as upper thread end contact region 40 and lower thread end contact region 42, respectively.

The smooth, curved contact regions 40 and 42 are particularly important in that the curved surface is much less likely to induce a stress concentration in the bone when the implant is subjected to loads; and the bone which grows-in to follow the curved surface is more naturally shaped and stronger than with sharply angled threaded surfaces.

FIG. 6 is a side view showing an alternate arrangement of a device constructed in accordance with the principles of the present invention. As shown in FIG. 6, the device is designated device 44. Device 44 includes engagement section 12 and anchorage section 46. Anchorage section 46 has a plurality of fin sections 48 disposed along at least a portion of the length of outer face 24 along shaft 16. Each of fin sections 48 is coaxial with shaft 16 and protrudes from shaft 16, i.e. the diameter of each of fin sections 48 is greater than the diameter of outer face 24 at the respective point where a fin section 48 is disposed.

The curved, i.e. radial characteristics of the region of contact between fin section 48 and shaft 16 is similar to that described above with respect to the first arrangement, i.e. implant device 10. In other words, each fin section 48 includes a top face 50 and a bottom face 52, each of which are in curved contact with outer face 24 at one end and are either in curved contact or contact at a point with end face 54 at opposite end regions thereof. Further, end face 54 is substantially parallel with outer face 24. Device 44 is suitable for use as a dental implant or orthopedic implant; the significant difference between the two uses being the dimensions of the device. Suitable dimensions for device 44 are substantially similar to those described above with respect to device 10.

The present invention advantageously provides an implant having threaded or finned portions which are provided with curved contact regions to provide the advantages described above. In addition, as noted above, the flat lower face 28 of each thread and the sloped upper face 26 provide a space into which bone grows. Significantly, the bone/thread interface is substantially flat to permit compression loading of the bone by the implant which results in healthier bone than if the bone were not subjected to compression loading. Further, the "wedge" shaped space (when viewed in cross-section) defined by the upper and lower faces allows for better in-growth and vascular growth through the bone than would be provided by a uniform, "rectangular" recess.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A fixation device at least partially implantable into tissue, comprising:
   a shaft having an outer face;
   a threaded portion wound around the outer face and forming a helical groove, at least a part of the threaded portion being implantable into tissue, the threaded portion comprising:
      a first face having:
         a first end portion in curved contact with the outer face;
         a second end portion opposite the first end portion;
      a second face being substantially flat and substantially perpendicular with the outer face, the second face having:
         a third end portion in curved contact with the outer face;
         a fourth end portion opposite the third end portion; and
      a third face, the third face being coupled to the second end portion and the fourth end portion and being substantially parallel with the outer face, wherein the third face is substantially perpendicular with the second face,
      wherein the helical groove is substantially flat.

2. A fixation device at least partially implantable into tissue, comprising:
   a shaft having an outer face;
   a threaded portion wound around the outer face and forming a helical groove, at least a part of the threaded portion being implantable into tissue, the threaded portion comprising:
      a first face having:
         a first end portion in curved contact with the outer face;
         a second end portion opposite the first end portion;
      a second face being substantially flat and substantially perpendicular with the outer face, the second face having:
         a third end portion in curved contact with the outer face;
         a fourth end portion opposite the third end portion; and
      a third face, the third face being coupled to the second end portion and the fourth end portion and being substantially parallel with the outer face, wherein the third face is substantially perpendicular with the second face,
      wherein the second end portion of the first face is in curved contact with the third face.

3. A fixation device at least partially implantable into tissue, comprising:
   a shaft having an outer face;
   a threaded portion wound around the outer face and forming a helical groove, at least a part of the threaded portion being implantable into tissue, the threaded portion comprising:
      a first face having:
         a first end portion in curved contact with the outer face;
         a second end portion opposite the first end portion;
      a second face being substantially flat and substantially perpendicular with the outer face, the second face having:
         a third end portion in curved contact with the outer face;
      a fourth end portion opposite the third end portion; and
      a third face, the third face being coupled to the second end portion and the fourth end portion and being substantially parallel with the outer face, wherein the third face is substantially perpendicular with the second face,
      wherein the fourth end portion of the second face is in curved contact with the third face.

* * * * *